(12) United States Patent
Van Krieken

(10) Patent No.: US 8,440,860 B2
(45) Date of Patent: May 14, 2013

(54) PROCESS FOR MANUFACTURING N, N-DIALKYL LACTAMIDE

(75) Inventor: Jan Van Krieken, Gorinchem (NL)

(73) Assignee: Purac Biochem BV, Gorinchem (NL)

( * ) Notice: Subject to any disclaimer, the term of this patent is extended or adjusted under 35 U.S.C. 154(b) by 248 days.

(21) Appl. No.: 13/121,275

(22) PCT Filed: Sep. 30, 2009

(86) PCT No.: PCT/EP2009/062683
§ 371 (c)(1),
(2), (4) Date: Apr. 1, 2011

(87) PCT Pub. No.: WO2010/037776
PCT Pub. Date: Apr. 8, 2010

(65) Prior Publication Data
US 2011/0178339 A1 Jul. 21, 2011

Related U.S. Application Data

(60) Provisional application No. 61/136,758, filed on Oct. 1, 2008.

(30) Foreign Application Priority Data

Oct. 1, 2008 (EP) ..................................... 08165639

(51) Int. Cl.
*C07C 231/02* (2006.01)
(52) U.S. Cl.
USPC ............ 564/134; 564/133; 564/201; 564/203
(58) Field of Classification Search .................. 564/133, 564/134, 201, 203
See application file for complete search history.

(56) References Cited

U.S. PATENT DOCUMENTS
2005/0222458 A1 10/2005 Craciun et al.

FOREIGN PATENT DOCUMENTS
| EP | 0 628 533 A1 | 12/1994 |
| WO | WO 2006/124899 A2 | 11/2006 |
| WO | WO 2007/107745 A2 | 9/2007 |

OTHER PUBLICATIONS

G. A. Brine et al., p-Hydroxymethadone: Synthesis, Crystal Structure and CD Properties, J. Chem. Soc., Perk. Trans. 1 : Org. Chem., 1991, vol. 8, pp. 1809-1814.*
Y. Kobayashi et al., *An Improved Synthetic Method of (S)-2-Alkoxypropanals from Ethyl(S)-Lactate*, Bull. Chem. Soc. Jpn., 62, 1989, vol. 62, No. 9, pp. 3038-3040.
G. R. Wolf et al., *Effect of Structure on Reactivity. X. Effect of α-Hydroxy Substituted Amides on the Ammonolysis and Hydrolysis of Methyl Acetate*, Journal of the American Chemical Society, vol. 78, 1956, pp. 4372-4373.
M. L. Fein et al., *N-Substituted Lactamides*, Journal of the American Chemical Society, 1953, vol. 75, pp. 2097-2099.
W. P. Ratchford et al., *Preparation of N-Substituted Lactamides by Aminolysis of Methyl Lactate*, J. Org. Chem., vol. 15, 1950, pp. 317-325.
W. P. Ratchford et al., *Preparation of N,N-Dimethylacrylamide by Pyrolysis of N,N-Dimethyl-α-Acetoxypropionamide*, Journal of the American Chemical Society, Aug. 1947, vol. 69, pp. 1911-1914.
J. L. Rao et al. *Cathodically Electrodepositable Novel Coating System from Castor Oil*, Journal of Applied Polymer Science, 1992, vol. 44, No. 11, pp. 1873-1881.
G. A. Brine et al., *p-Hydroxymethadone: Synthesis, Crystal Structure and CD Properties*, J. Chem. Soc., Perk. Trans. 1: Org. and Bio-Org. Chem., 1991, vol. 8, pp. 1809-1814.
Nov. 5, 2009 International Search Report issued in PCT/EP2009/062683.
Nov. 5, 2009 Written Opinion issued in PCT/EP2009/062683.

* cited by examiner

*Primary Examiner* — Shailendra Kumar
(74) *Attorney, Agent, or Firm* — Oliff & Berridge, PLC

(57) ABSTRACT

A process for manufacturing dialkyl lactamide including reacting lactide and dialkylamine selected from one or more of dimethylamine, diethylamine, and methylethylamine to form a reaction mixture which includes dialkyl lactamide selected from N,N-dimethyl lactamide, N,N-diethyl lactamide, and N,N-methylethyl lactamide, N,N-dialkyl lactoyl lactamide, and dialkylamine, subjecting the reaction mixture to a separation step to form a product stream including N,N-dialkyl lactamide, a first recycle stream including dialkylamine and a second recycle stream including N,N-dialkyl lactoyl lactamide, feeding the recycle streams to the reaction step, and isolating the product stream. The process allows the manufacture of N,N-dimethyl lactamide, N,N-diethyl lactamide, and N,N-methylethyl lactamide on a commercial scale.

11 Claims, 1 Drawing Sheet

PROCESS FOR MANUFACTURING N,N-DIALKYL LACTAMIDE

The present invention pertains to a process for manufacturing N,N-dialkyl lactamide, in particular dimethyl lactamide, diethyllactamide, and methylethyl lactamide.

N,N-dialkyl lactamides are known in the art. They have a number of uses, e.g., as solvent and chemical intermediate.

Various methods for synthesising N,N-dialkyl lactamides, e.g. dimethyl lactamide, have been described in the art.

WO 2007/107745 describes the use of lactamide compounds to reduce the toxicity of other compounds present in, e.g., agrochemical formulations. It is indicated that the compounds may be prepared by reacting a lactate ester, e.g., ethyl lactate, or a lactide with a dialkylamine. The examples are all at laboratory scale, and many of them show long reaction times.

Kobayashi (Y. Kobayashi, M. Takase, Y. Ito, S. Terashima, An improved synthetic method of (S)-2-alkoxypropanals from ethyl(S)lactate, Bull. Chem. Soc. Jpn., 62, 3038-3040 (1989) Vol. 62, No. 9) prepared dimethyl lactamide on laboratory scale by reaction of anhydrous dimethylamine with ethyl lactate in a sealed bottle at 70° C. for 2 days. The product was purified by distillation. A yield of 93% was reported.

Wolf (G. R. Wolf, J. G. Miller, A. R. Day, Effect of structure on reactivity. X. Effect of α-hydroxy substituted amides on the ammonolysis and hydrolysis of methyl acetate, J. Am. Soc., Vol. 78, 1956, 4372-4373) prepared dimethyl lactamide by aminolysis of ethyl lactate with dimethyl amine in anhydrous methanol. Dimethyl lactamide was purified by distillation.

Fein (Fein, M. L.; Filachione, E. M., N-Substituted lactamides, Journal of the American Chemical Society (1953), 2097-9) reported that dimethyl amine reacted readily at room temperature with methyl lactate, while dibutyl amine did not. For the higher dialkyl amines the route of dehydration of dialkyl ammonium lactate was advised.

Ratchford (W. P. Ratchford, C. H. Fisher, Preparation of n-substituted lactamides by aminolysis of methyl lactate, J. Org. Chem., Vol. 15, 1950, 317-325) showed that dimethyl amine reacted readily with methyl lactate towards dimethyl lactamide at 35° C., while diethyl amine did not react easily.

Ratchford (Ratchford, W. P.; Fisher, C. H., Preparation of N,N-dimethylacrylamide by pyrolysis of N,N-dimethyl-alpha-acetoxypropionamide, Journal of the American Chemical Society (1947), 69 1911-14) prepared dimethyl lactamide from methyl lactate and dimethyl amine, with sulphuric acid as catalyst. The reaction took 3 weeks at room temperature to result in a yield of 86% after distillation.

US 2005/222458 mentions lactic acid, lactate esters, oligolactic acid and lactide as possible feedstocks for lactamide production. The examples are on laboratory scale (samples of the order of grams).

Rao (J. L. Rao, R. S. Balakrishna, M. M. Shirsalkar, Cathodically electrodepositable novel coating system from castor oil, Journal of Applied Polymer Science (1992), 44(11), 1873-81) prepared diethyl lactamide from lactic acid and diethyl amine. The water formed during the reaction was distilled off azeotropically with toluene at 110° C.

EP 628533 describes depolymerisation of polylactic acid from trash by means of reaction with water, alcohols or amines. All kinds of primary and secondary amines and diamines were used to result in lactamides. Reaction times up to 3 hour and temperatures of 75-170° C. are mentioned. Dimethyl amine and diethyl amine are used in the examples, with a temperature of 75-100° C. and a reaction time of 0.75-1 hour.

WO2006/124899 relates to processes for the production of derivatives of lactides. Lactamides are mentioned as one of the possible compounds to be prepared.

Brine (G. A. Brine, K. G. Boldt, D. Prakash, D. J. Kotchmar, V. C. Bondeson, D. J. Bradley, P. Singh, F. I. Carroll, p-Hydroxymethadone: synthesis, crystal structure and CD properties, J. Chem. Soc., Perk. Trans. 1: Org. and Bio-Org. Chem. (1972-1999) (1991), (8), 1809-14) prepared dimethyl lactamide from (S)-dilactide and dimethyl amine in a 1 L Parr flask (pressure reactor). After reacting for 1 hour at 40° C. and a cooling overnight, distillation resulted in 77.5% yield of dimethyl lactamide as water white liquid.

However, most of the references discussed above only describe the production of N,N-dialkyl lactamide on laboratory scale. On laboratory scale, it typically is not feasible to develop an energy-efficient process and/or to develop a process achieving a 100% conversion of reactants to end product.

There is need for a commercially applicable process for the manufacture of N,N-dialkyl lactamide, in particular N,N-dimethyl lactamide, N,N-diethyl lactamide, and N,N-methylethyl lactamide, which meets the following requirements: The process should be fast and energy-efficient. It should yield relatively few by-products. It should be relatively simple to keep the investment costs relatively low.

The present invention provides a process in which these requirements are met. Further advantages of the process according to the invention will become clear from the further specification.

The present invention provides a process for manufacturing dialkyl lactamide comprising the steps of reacting lactide and dialkylamine selected from one or more of dimethylamine, diethylamine, and methylethylamine to form a reaction mixture which comprises dialkyl lactamide selected from N,N-dimethyl lactamide, N,N-diethyl lactamide, and N,N-methylethyl lactamide, N,N-dialkyl lactoyl lactamide, and dialkylamine, subjecting the reaction mixture to a separation step to form a product stream comprising N,N-dialkyl lactamide, a first recycle stream comprising dialkylamine and a second recycle stream comprising N,N-dialkyl lactoyl lactamide, feeding the recycle streams to the reaction step, and isolating the product stream.

The process preferably is carried out continuously, with the separation step being carried out in a separation section comprising two separation units. In a continuous process as described herein, any heat released in the reaction section may efficiently be utilized in the separation section, allowing high energy efficiency. In addition, optimal allocation of recycle streams is possible, allowing maximum conversion of reactants to product, even (close to) a 100% conversion.

The dialkylamine used in the present invention is selected from one or more of dimethylamine, diethylamine, and methylethylamine. In the following, the word dialkylamine will be used to encompass all of these components, unless another meaning is evident from the context.

These particular amines have been found to be difficult to process, because the difference in boiling point between the amine, the lactide starting material and the product N,N-dialkyl lactamide. The present invention provides a solution to this problem.

The lactide used in the present invention may be any one of D-lactide, meso-lactide, L-lactide, or mixtures thereof.

In the reaction step of the process according to the invention lactide and dialkylamine selected from dimethylamine, diethylamine, and methylethylamine are reacted to form a reaction mixture which comprises product N,N-dialkyl lactamide, together with intermediate N,N-dialkyl lactoyl lactamide, and starting dialkylamine. Minor amounts of higher oligomers than N,N-dialkyl lactoyl lactamide may also be formed.

Lactide has a melting point of 35-97° C., depending on the stereochemical composition. Dimethylamine has an atmospheric boiling point of about 7° C., diethylamine has an atmospheric boiling point of about 56° C. Methylethylamine has an atmospheric boiling point of about 37° C. Accordingly, special measures are required to allow the two components to react. More in particular, the reaction step of the process according to the invention is generally carried out at such a temperature and pressure that the lactide, the dialkylamine, and the N,N-dialkyl lactamide are in the liquid phase. This will be elucidated in more detail below.

The overall molar ratio in the reaction step between dialkylamine and lactide is in the range of 1.5:1 to 10:1. It is preferred for the reaction to be carried out at a slight excess of dialkylamine, to prevent formation of amides of lactide polymers or oligomers. Therefore, in one embodiment, the molar ratio between dialkylamine and lactide is in the range of 2.0:1 to 4.0:1, more in particular in the range of 2.1:1 to 2.5:1.

DETAILED DESCRIPTION OF EMBODIMENTS

In one embodiment of the present invention, the process is carried out continuously with the reaction step being carried out in a reaction section comprising two reactors and the separation step being carried out in a separation section comprising two separation units.

Figure 1:
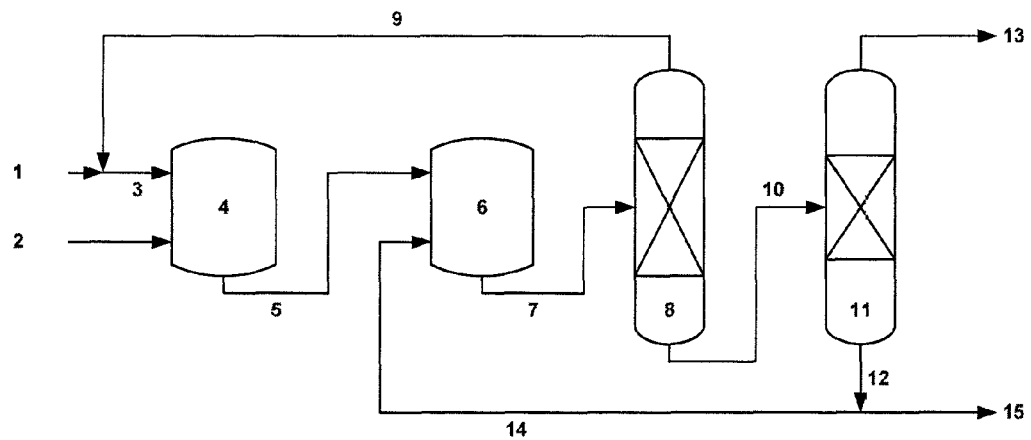
FIG. 1 illustrates a process for manufacturing dialkyl lactamide that is carried out continuously with the reaction step being carried out in a reaction section comprising two reactors and the separation step being carried out in a separation section comprising two separation units.

This embodiment will be elucidated with reference to FIG. 1, without being limited to this specific embodiment.

In FIG. 1 a dialkylamine feed (1) is combined with dialkylamine from a recycle stream (9) to form a combined dialkylamine stream (3), which, together with a lactide feed (2) is fed to a first reactor (4), where dialkylamine is reacted with lactide to form N,N-dialkyl lactoyl lactamide and some N,N-dialkyl lactamide. An effluent stream (5) comprising N,N-dialkyl lactamide, N,N-dialkyl lactoyl lactamide, and dialkylamine is led to a second reactor (6), where N,N-dialkyl lactoyl lactamide is converted to N,N-dialkyl lactamide. Effluent stream (7), comprising N,N-dialkyl lactamide, N,N-dialkyl lactoyl lactamide, and dialkylamine, is fed to a first separation unit (8). In this unit, the mixture is separated to form a top stream (9) comprising dialkylamine, which is recycled back to the first reactor. The bottom stream (10) which comprises N,N-dialkyl lactoyl lactamide and N,N-dialkyl lactamide is fed to second separation unit (11), where it is separated to form a product stream (13) comprising N,N-dialkyl lactamide, and a bottom recycle stream (12) comprising N,N-dialkyl lactoyl lactamide. From bottom recycle stream (12) a minor purge stream of coloured components (15) is removed, and the remaining bottom stream (14) is recycled back to the second reactor.

While not wishing to be bound by any theory, the inventor has recognised that the reaction of dialkylamine with lactide is through a two-step-reaction. In the first step, one mole of lactide reacts with one mole of dialkylamine to form N,N-dialkyllactoyllactamide. This reaction is exothermic and takes place at a high reaction rate. In the second step, the N,N-dialkyllactoyllactamide reacts with further dialkylamine to form N,N-dialkyl lactamide. The second reaction is also exothermic, but takes place at a lower reaction rate. In the present embodiment it is the intention to carry out the first step of the reaction, reaction of lactide with dialkylamine to form N,N-dialkyllactoyllactamide in the first reactor, and the second step, the reaction of N,N-dialkyllactoyllactamide with further dialkylamine to form N,N-dialkyl lactamide mainly in the second reactor.

The first reactor generally is operated at a pressure of 1-20 bar and a temperature of 0-200° C. More in particular, the pressure may be in the range of 5 to 15 bar. It may be desired to keep the temperature at a value between 40 and 200° C., in particular between 100 and 175° C. For a reaction temperature of 100-150° C., a preferred pressure range is 5-15 bar. Operating at low pressure, e.g., in the range of 1-2 bar is possible where the reaction temperature is kept low, e.g., below 50° C.

The second reactor is generally operated at a pressure of 1-10 bar. The temperature in the second reactor is generally kept at a value between 50 and 200° C., in particular between 100 and 150° C., to keep the reaction rate sufficiently high.

The residence time in the first reactor will generally be between 5 seconds and 15 minutes, more in particular between 30 seconds and 10 minutes, still more in particular between 30 seconds and 5 minutes. The residence time in the second reactor will generally be between 15 and 600 minutes, more in particular between 15 and 300 minutes, still more in particular between 30 and 120 minutes.

The volume of the first reactor may be much smaller than the volume of the second reactor, this in view of the shorter residence time in the first reactor than in the second reactor. In one embodiment the ratio between the volume of the first reactor to the volume of the second reactor is at least 1:2, more in particular at least 1:5. The ratio will generally be at most 1:500.

The nature of the reactors is generally not critical to the present invention. The first reactor may, for example, be a static mixer. The second reactor may, for example, be a stirred tank reactor or a plug flow reactor.

Depending on process parameters like residence time, conversion, and reaction rate, the volume of the first reactor may be in the range of 0.5-25 liter per ktonne, such as 0.5-10 liter per ktonne, product per year. The volume of the second reactor may be in the range of 200-1000 liter per ktonne product per year.

In this embodiment, the separation section comprises two separation units, wherein in the first separation unit dialkylamine is separated off, and in the second separation unit N,N-dialkyl lactoyl lactamide is separated from N,N-dialkyl lactamide.

In this embodiment, the first separation unit may any conventional separation unit, for example, a flash drum or a distillation unit. It is within the scope of the skilled person to determine suitable pressure. A suitable pressure will generally be in the range of 0.02-3 bar, such as 0.1-3 bar. The first separation unit will generally have 1 to 2 theoretical trays.

In the second separation unit, the N,N-dialkyl lactoyl lactamide is separated from N,N-dialkyl lactamide. This separation step is conveniently carried out in a distillation unit, where the N,N-dialkyl lactamide is recovered as top product.

Given the atmospheric boiling point of these compounds (for example 222° C. for dimethyl lactamide) it may be preferred to carry out the distillation at reduced pressure, for example in the range of 5-100 mbar. The second separation unit will generally have 1 to 6 theoretical trays, more in particular 3-5 theoretical trays.

The process generates a dialkylamine recycle stream and a N,N-dialkyl lactoyl lactamide recycle stream, both of which are recycled to the reaction section.

The dialkylamine can be recycled to the first reactor, to the second reactor, or to both. Recycling to the first reactor may sometimes be attractive for reasons of process efficiency. The recycle stream comprising N,N-dialkyl lactoyl lactamide is recycled to the second reactor.

The heat generated in the reaction section, especially in the first reactor, may efficiently be utilized in the further process, for instance in the first separation unit.

In another embodiment of the present invention, the process is carried out continuously with the reaction step being carried out in a reaction section comprising one reactor and the separation step being carried out in a separation section comprising two separation units.

In this embodiment, the lactide and the dialkylamine are added continuously to a reactor which already contains a reaction mixture comprising dialkylamine, N,N-dialkyl lactamide, and N,N-dialkyllactoyllactamide in the liquid state.

Figure 2:
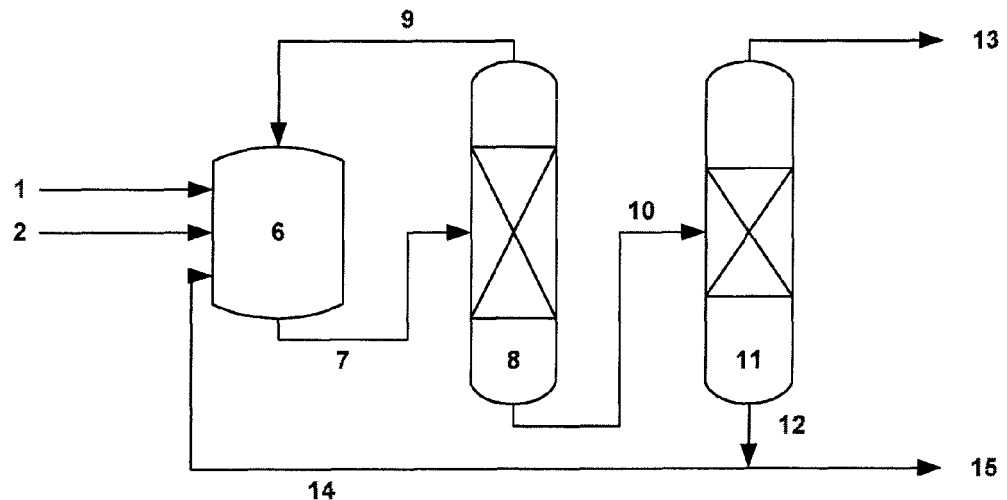
FIG. 2 illustrates a process for manufacturing dialkyl lactamide that is carried out continuously with the reaction step being carried out in a reaction section comprising one reactor and the separation step being carried out in a separation section comprising two separation units.

This embodiment will be elucidated with reference to FIG. 2, without being limited thereto or thereby.

In FIG. 2 a dialkylamine feed (1) and a lactide feed (2) are fed to a reactor (6). Effluent stream (7), comprising N,N-dialkyl lactamide, N,N-dialkyl lactoyl lactamide, and dialkylamine is fed to a first separation unit (8). In this unit, the mixture is separated to form a top stream (9) comprising dialkylamine, which is recycled back to the reactor. The bottom stream (10) which comprises N,N-dialkyl lactoyl lactamide and N,N-dialkyl lactamide is fed to second separation unit (11), where it is separated to form a product stream (13) comprising N,N-dialkyl lactamide, and a bottom recycle stream (12) comprising N,N-dialkyl lactoyl lactamide. From bottom recycle stream (12) a minor purge stream of coloured components (15) is removed, and the remaining bottom stream (14) is recycled back to the reactor.

In one embodiment the reactor is operated at a pressure of 1-10 bar. In this embodiment, the temperature in the reactor is generally kept at a value between 100 and 200° C., in particular between 100 and 150° C., to keep the reaction rate sufficiently high. The residence time in the reactor will generally be between 15 and 300 minutes, more in particular between 15 and 200 minutes, still more in particular between 30 seconds and 90 minutes. The reactor may, for example, be a stirred tank reactor or a plug flow reactor.

Depending on process parameters like residence time, conversion, and reaction rate, the volume of the reactor may be in the range of 200-1000 liter per ktonne product per year.

For a more detailed description of the separation and recycle steps reference is made to what has been stated above for the embodiment with two reactors, the only difference being that in the present case both the dialkylamine and the N,N-dialkyl lactoyl lactamide are recycled to the one reactor.

In one embodiment of the present invention, the N,N-dialkyl lactamide is dimethyl lactamide and the dialkylamine is dimethylamine. The use of the embodiment with two reactors may be particularly preferred, because it allows easier processing of the heat formed during reaction.

In another embodiment of the present invention, the N,N-dialkyl lactamide is N,N-diethyl lactamide and the dialkylamine is diethylamine, or the N,N-dialkyl lactamide is N,N-methylethyl lactamine and the dialkylamine is methylethylamine. Compared to dimethylamine, diethylamine has an atmospheric boiling point which is substantially higher. This means that in general, the pressure required to keep all components in the liquid phase is lower than when dimethylamine is used.

The present invention is illustrated by the following examples, without being limited thereto or thereby.

Example 1

Reaction of Dimethylamine and Lactide to form N,N-dimethyl lactoyl lactamide

This example illustrates the first step of the process according to the invention. A 250 ml roundbottom flask was equipped with a reflux condensor which was cooled at −60° C. The flask was charged with 100 g of solid L-lactide and a small magnetic stirring egg. Within 14 minutes 73 g (2.3 equivalents) of anhydrous dimethyl amine was added, while stirring magnetically. The reaction mixture was kept at a temperature of 20-30° C. To avoid a too high increase in temperature, the flask was cooled by means of an ice-bath. Shortly after addition of all of the dimethyl amine, the lactide had dissolved/reacted completely.

Analysis by GLC showed complete conversion of lactide into N,N-dimethyl lactoyl lactamide (70%) and a small amount of N,N-dimethyl lactamide (7%). The remainder was mainly unreacted dimethyl amine.

Example 2

Reaction of Dimethylamine and Lactide to form N,N-dimethyl lactamide

Analogous to example 1, a reaction mixture was prepared from 25 g of L-lactide and 18 g of dimethyl amine. To illustrate the second reaction step of the process of the invention, the resulting product contained N,N-dimethyl lactoyl lactamide, unreacted dimethylamine, and a small amount of N,N-dimethyl lactamide (7%). Small sample flasks of 2 ml were filled with reaction mixture, closed carefully and thermostated at 76° C. In time flasks were cooled and analysed by GLC. The results are presented in Table 1.

TABLE 1

| GLC analysis of reaction mixtures after varying periods of time | |
|---|---|
| Sample time (hr) | Concentration of DML (wt %, GLC) |
| 0 | 2.5 |
| 0.25 | 23.6 |
| 0.5 | 40.6 |
| 1 | 57.2 |
| 2 | 67.2 |
| 3 | 73.4 |
| 5 | 82.5 |
| 7.17 | 85.8 |

Example 3

Analogous to example 2, more kinetic experiments were conducted with a comparable starting composition at a temperature of 50° and 103° C. The results of GLC analysis of the reaction mixtures is indicated in Table 2.

TABLE 2

GLC analysis of reaction mixtures after varying periods of time

| Time | Concentration of DML (wt %, GLC) | |
|---|---|---|
| (hr) | 50° C. | 103° C. |
| 0 | 2.5 | 49.3 |
| 0.5 | 18.4 | 68.2 |
| 1 | 30.3 | 74.3 |
| 2 | 44.6 | 79.0 |
| 3 | 52.2 | |
| 4 | 60.4 | 84.6 |
| 5 | 66.8 | |
| 7 | | 87.7 |
| 7.22 | 69.0 | |

From these data the kinetic parameters (energy of activation and pre-exponential factor) of the second reaction were determined by fitting in Aspen®. Using these data a kinetic model was made in Aspen®. This kinetic model was included in a process model and the process of FIG. 1 was simulated at industrial scale.

The following settings of the process model were applied:

| | Reactor 1 | Reactor 2 | Column 1 | Column 2 |
|---|---|---|---|---|
| Volume (m³) | 0.5 | 15 | | |
| Pressure (bar) | 20 | 5 | 0.050 | 0.020 |
| Temperature (° C.) | 120 | 120 | | |
| Type | CSTR | CSTR | 2 theoretical stages | 4 theoretical stages |
| DMA in bottom | | | <10 ppm | |
| DML in top | | | | >99.9 wt % |

The temperature resulting from the simulation in Column 1 was 110° C. (top) and 130° C. (bottom) and in Column 2 was 105° C. (top) and 130° C. (bottom). The residence time was 0.14 h in reactor 1 and 3.5 h in reactor 2.

This simulation resulted in a production capacity of 2600 kg/hr and a DML yield of 100%.

The invention claimed is:

1. Process for manufacturing dialkyl lactamide, the process comprising the steps of:
    reacting lactide and dialkylamine selected from one or more of dimethylamine, diethylamine, and methylethylamine to form a reaction mixture which comprises dialkyl lactamide selected from N,N-dimethyl lactamide, N,N-diethyl lactamide, and N,N-methylethyl lactamide, N,N-dialkyl lactoyl lactamide, and dialkylamine,
    subjecting the reaction mixture to a separation step to form a product stream comprising N,N-dialkyl lactamide, a first recycle stream comprising dialkylamine and a second recycle stream comprising N,N-dialkyl lactoyl lactamide,
    feeding the recycle streams to the reaction step, and
    isolating the product stream.

2. Process according to claim 1, wherein in the reaction step the molar ratio between dialkylamine and lactide is in the range of 1.5:1 to 10:1.

3. Process according to claim 1, wherein the pressure in the reaction step is selected to be such that the lactide, the dialkylamine, and the N,N-dialkyl lactamide are in the liquid phase.

4. Process according to claim 1, wherein the N,N-dialkyl lactamide is dimethyl lactamide and the dialkylamine is dimethylamine.

5. Process according to claim 1, wherein the N,N-dialkyl lactamide is N,N-diethyl lactamide and the dialkylamine is diethylamine, or the N,N-dialkyl lactamide is N,N-methylethyl lactamine and the dialkylamine is methylethylamine.

6. Process according to claim 1, wherein the process is carried out continuously, the separation step being carried out in a separation section comprising two separation units.

7. Process according to claim 6, wherein the reaction step is carried out in a reaction section comprising two reactors.

8. Process according to claim 7, wherein the residence time in the first reactor is shorter than the residence time in the second reactor, and the reactor volume of the first reactor is smaller than the reactor volume of the second reactor.

9. Process according to claim 7, wherein the recycle stream comprising N,N-dialkyl lactoyl lactamide is fed to the second reactor and the recycle stream comprising dialkylamine is fed to the first reactor.

10. Process according claim 6, wherein the reaction step is carried out in a reaction section comprising one reactor.

11. Process according to claim 6, wherein in the first separation unit dialkylamine is separated off, and in the second separation unit N,N-dialkyl lactoyl lactamide is separated from N,N-dialkyl lactamide.

* * * * *